United States Patent
Bhargav et al.

(10) Patent No.: US 9,880,093 B2
(45) Date of Patent: Jan. 30, 2018

(54) OPTICAL ABSORPTION MONITOR SYSTEM

(71) Applicant: GE Healthcare Bio-Sciences AB, Uppsala (SE)

(72) Inventors: Anoop Bhargav, Bangalore (IN); Jeganathan Srinivasan, Bangalore (IN)

(73) Assignee: GE Healthcare Bio-Sciences AB, Uppsala (SE)

( * ) Notice: Subject to any disclaimer, the term of this patent is extended or adjusted under 35 U.S.C. 154(b) by 0 days.

(21) Appl. No.: 15/024,593

(22) PCT Filed: Sep. 18, 2014

(86) PCT No.: PCT/EP2014/069865
§ 371 (c)(1),
(2) Date: Mar. 24, 2016

(87) PCT Pub. No.: WO2015/044020
PCT Pub. Date: Apr. 2, 2015

(65) Prior Publication Data
US 2016/0231232 A1    Aug. 11, 2016

(30) Foreign Application Priority Data

Sep. 24, 2013   (IN) .......................... 2812/DEL/2013

(51) Int. Cl.
*G01N 21/00*   (2006.01)
*G01N 21/33*   (2006.01)
(Continued)

(52) U.S. Cl.
CPC ............ *G01N 21/33* (2013.01); *G01N 21/05* (2013.01); *G01N 21/274* (2013.01); *G01N 2201/062* (2013.01); *G01N 2201/0624* (2013.01)

(58) Field of Classification Search
CPC ....... G01N 21/33; G01N 21/05; G01N 21/274
See application file for complete search history.

(56) References Cited

U.S. PATENT DOCUMENTS 5,078,497 A * 1/1992 Borton .................. G01N 21/55
356/445
5,452,076 A * 9/1995 Schopper ............. G01F 23/292
356/128

(Continued)

FOREIGN PATENT DOCUMENTS

EP     1647820 A2 *  4/2006  ............... G01J 3/42
WO  2013/064973 A1   5/2013

OTHER PUBLICATIONS

International Search Report and Written Opinion for International Application No. PCT/EP2014/069865, dated Mar. 17, 2015, 17 pages.

(Continued)

*Primary Examiner* — Casey Bryant
(74) *Attorney, Agent, or Firm* — Wood IP LLC (57) ABSTRACT

Absorption monitor system comprising a light source and a light detector arranged so as to define an absorption detection light path there between, and a controller arranged to control the operation of the light source, wherein the light source comprises a Light Emitting Diode capable of emitting light in the UV range (UV-LED) and wherein the absorption monitor system does not comprise a reference light-detector and the controller is arranged to compensate for fluctuations in light output intensity from the UV-LED.

9 Claims, 7 Drawing Sheets

(51) Int. Cl.
*G01N 21/27* (2006.01)
*G01N 21/05* (2006.01)

(56) References Cited

U.S. PATENT DOCUMENTS

| | | | |
|---|---|---|---|
| 8,068,227 B2* | 11/2011 | Tormod | G01N 21/05 356/432 |
| 2004/0104355 A1* | 6/2004 | DiFoggio | E21B 49/08 250/461.1 |
| 2005/0023536 A1* | 2/2005 | Shackle | H05B 33/0815 257/79 |
| 2017/0205336 A1* | 7/2017 | Ido | G01N 21/274 |

OTHER PUBLICATIONS

Maxim Shatalov et al: "Reliablitiy of AlGaN-based deep UV LEDs on sapphire", Proceedings of SPIE, vol. 6134, Feb. 9, 2006 (Feb. 9, 2006), p. 61340P, XP055114215, ISSN: 0277-786X, DOI: 10.1117/12.647204 abstract; section 4.2.

* cited by examiner

OPTICAL ABSORPTION MONITOR SYSTEM

CROSS-REFERENCE TO RELATED APPLICATIONS

This application is a filing under 35 U.S.C. 371 of international application number PCT/EP2014/069865, filed Sep. 18, 2014, which claims priority to Indian application number 2812/DEL/2013, filed Sep. 24, 2013, the entire disclosures of each of which are hereby incorporated by reference.

FIELD OF THE INVENTION

The present disclosure relates to an optical absorption monitor system and in particular to a flow cell absorption monitor system.

BACKGROUND

Many substances absorb ultra violet or visible light due to their chemical composition. The absorption of light by substances has been used as the basis for detecting the presence of, and for measuring the concentration of, such substances for many years. The concentration of the substance can be determined by use of the Beer Lambert Law:

$$A = Ebc$$

where A is absorbance,
E is the molar absorbtivity with units of L mol-1 cm-1,
b is the path length of the sample defined in cm; and
c is the concentration of the compound in solution, expressed in mol L-1

The Emax represents the maximum absorption of a substance at a given wavelength.

An absorption monitor system typically comprises a light source for providing light of one or more wavelengths to a fluid sample and an optical detection system for detecting any interaction between the light and the sample. The fluid sample may either be a static sample in a suitable container provided with windows for the optical absorbance measurement or the fluid sample is provided as a fluid flow in a flow cell, as will be disclosed in more detail below. Still further, the monitor system may be of immersion type, wherein optical components of the system are immersed into the fluid sample and are arranged to define an optical detection path there between.

One example of an absorption monitor system is a flow cell UV absorption monitor system that is utilized to measure different absorbance of light at various wavelengths in chromatography systems when separated molecules are eluted from the columns. However, flow cell UV absorption monitor systems may be used to selectively detect samples in a large range of applications other than chromatography systems, such as production fluid process systems, laboratory systems, analytical systems, etc. Monitor systems of this type usually include a light source, a flow cell and a light detector. Ideally, the components of the monitor system are selected and designed to ensure a signal-to-noise ratio with minimal drift and refractive index sensitivity. The light source is typically comprised of a mercury-lamp, a deuterium lamp or a xenon flash lamp. However, in recent years monitor systems using a UV-LED (Light Emitting Diode capable of emitting light in the UV range) as light source have been developed. One example of an UV-LED based monitor system is disclosed in U.S. Pat. No. 8,068,227.

In order to achieve a signal-to-noise ratio with minimal drift and refractive index sensitivity according to above, monitor systems of this type are regularly provided with a reference light detector for registering fluctuations and/or drift in light intensity output from the light source. The output from the reference light detector is used to reduce the influence of such fluctuations etc. by normalization or the like of the output from the monitor system.

As is disclosed in U.S. Pat. No. 8,068,227, UV-LED based monitor systems may be more compact and less complex compared to monitor systems based on other light sources. Therefore, UV-LED based monitor systems are generally less expensive to manufacture. However, there is still a need for less complex and less expensive monitor systems.

SUMMARY OF THE INVENTION

The object of the invention is to provide a new absorption monitor system which overcomes one or more drawbacks of the prior art. This is achieved by the absorption monitor system as defined in the independent claim.

One advantage with the present absorption monitor system is that it provides signal-to-noise ratio with minimal drift and refractive index sensitivity while it is less complex compared to current systems and therefore less expensive.

Another advantage is that the present absorption monitor system is arranged to allow biasing the UV-LED at optimum point throughout the lifecycle of the UV-LED which will increase the life of the LED. As the UV-LED represents a significant part of the total cost of the monitor system, extending its life significantly impacts the total lifetime cost of the monitor system. Also, the controller will be aware of the bias point and hence will be able to predict the correct voltage range at the photo detector which will help in eliminating errors in reference due to absorbance by the presence of materials in the flow cell.

In one aspect there is provided an absorption monitor system comprising a light source and a light detector arranged so as to define an absorption detection light path there between, and a controller arranged to control the operation of the light source, wherein the light source comprises a Light Emitting Diode capable of emitting light in the UV range (UV-LED) and wherein the absorption monitor system does not comprise a reference light-detector and the controller is arranged to compensate for fluctuations in light output intensity from the UV-LED.

In one aspect the absorption monitor system comprises a temperature sensor for registering the temperature of the UV-LED, and wherein the controller is arranged to control the light output intensity from the UV-LED in response to the registered temperature to compensate for fluctuations in light output intensity from the UV-LED due to temperature changes.

In one aspect the absorption monitor system the controller is arranged to register the total time then the UV-LED is in operation (UV-age) and to control the light output intensity from the UV-LED in response to the registered UV-age to compensate for fluctuations in light output intensity from the UV-LED due to age.

In one aspect the absorption monitor system the controller is arranged to register and store a reference absorption signal for a sample with known absorption and to apply a reference correction to the absorption signal registered by the photo detector using the reference absorption signal.

In one aspect the absorption monitor system the controller is arranged to provide a warning signal when the reference absorption signal exceeds a predefined threshold.

In one aspect the absorption monitor system comprises a flow cell with a fluid flow channel and two opposing windows providing the absorption detection light path there between, one window arranged to receive light from the UV-LED and the other window arranged to output resulting light from the measurement light-path to the light detector.

A more complete understanding of the present invention, as well as further features and advantages thereof, will be obtained by reference to the following detailed description and drawings. However, it should be understood that the detailed description and specific examples while indicating preferred embodiments of the invention are given by way of illustration only. Various changes and modifications within the spirit and scope of the invention will become apparent to those skilled in the art from the detailed description below

DETAILED DESCRIPTION OF EMBODIMENTS OF THE INVENTION

As mentioned above, the absorption monitor system of present invention will be illustrated as a flow cell absorption monitor system, although it should be noted that the system may be of static type, immersion type or the like. The key feature is that there is an optical path for detection light through a representative volume of the sample to be analyzed.

Figure 1:
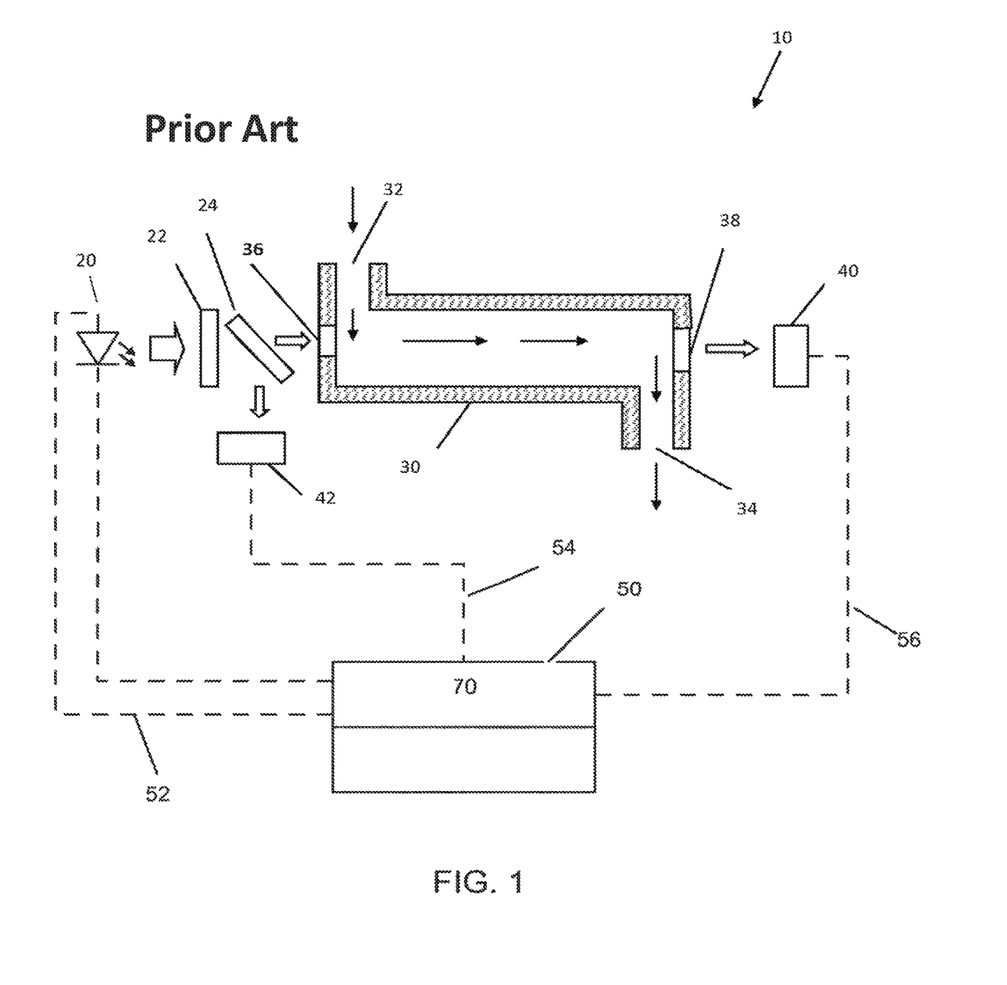
FIG. 1 is a schematic block diagram of a prior art absorption monitor system.

FIG. 1 is a schematic representation of a prior art absorption monitor system in the form of an UV-LED based flow cell absorption monitor system 10. The monitor system 10 generally comprises a light source in the form of an UV-LED 20, a flow cell 30, an absorption light detector 40, a reference light detector 42, and a controller 50. The UV-LED 20 may essentially be any type of UV-LED capable of emitting light in the desired UV spectra. In the disclosed embodiment, a band pass interference filter 22 is provided between the UV-LED 20 and an entrance window 36 in the flow cell 30. The band pass filter 22 is an optical filter that allows light of a predefined narrow wavelength range to pass while light of other wavelengths is prevented to pass. According to one embodiment the bandwidth of the filter is preferably less than 10 nm or lower, to give a good linearity and large dynamic range. According to an alternative embodiment, the band pass filter 22 may be omitted by selecting an UV-LED 20 with a sufficiently narrow emission spectra at the desired wavelength. Still alternatively, the light source 20 may be comprised of two or more UV-LEDs each providing light of a different wavelength, whereby a multi-wavelength monitor system 10 may be achieved.

The wavelength of UV light employed to irradiate the sample can be selected by either the use of an appropriate LED which emits at a specific wavelength of UV light (for example, a UVTOP® 260 nm or 280 nm LED) or by means of a light emitting diode with a broader emission spectrum in the deep UV. UVTOP® LEDs are available from Sensor Electronic Technology Inc., SC, USA (e.g. the 'TO-39' package contains a number of UV-light emitting diodes which emit in the range of 250-365 nm).

The light then passes through a beam-splitter 24 which diverts some of the light onto a reference photo detector 42 while the remainder is directed through the window 36 into the solution within the flow cell 10. The beam-splitter 24 and reference photo detector 42 are used to follow any intensity changes in the light emitting diode 20 and thus to provide a stable base line in the output data. The flow cell 30 with an inlet 32 and an outlet 34 has windows 36 and 38 which are made from a UV transparent material such as sapphire, quartz or synthetic fused silica and is of a known path length. which can either be UV sensitive photo multipliers or UV sensitive photo diodes A solution containing a fluid flow of sample (e.g. a protein or nucleic acid) is passed through the flow cell 30, as indicated by the single arrows, via the inlet 32 and the outlet 34. A UV light emitting diode 20 is used to irradiate the solution in the flow cell 30, the light entering the flow cell 30 through the UV transparent window 36, as indicated by the block arrows. Light passing through the solution (indicated by the block arrow) and window 38 is then detected by the photo-detector 40.

If desired, the concentration of the substance in the solution can then be determined by use of the Beer Lambert Law where the molar absorbtivity (E) of the substance is already known. Alternatively, the concentration of the substance can be determined by use of a dose-response curve which has previously been produced for the substance of interest at a given wavelength (e.g. 280 nm).

The controller 50 is arranged to control the UV light output from the UV-LED 20 by setting a desired bias current. In FIG. 1 the controller is connected to the UV-LED by communication line 52, which may be a direct current feed circuit, but alternatively there may be a separate UV-LED driver (not shown) which in turn is controlled by the controller 50, or the like as is appreciated by anyone skilled in the art. Similarly the photo-detector 40 and the reference detector 42 are connected to the controller 50 by communication lines 56 and 54 respectively, and the communication lines may be implemented in any suitable way enabling transfer of the registered light intensities from respective unit. The controller 50 is arranged to provide a reference-compensated output reflecting the absorbance of the sample fluid in the flow cell, and which output is compensated for fluctuations in the light output from the UV-LED 20. In one embodiment the controller 50 comprises a digital microcontroller circuit 70 comprising at least one digital to analog output arranged to control the operation of the UV-LED 20 and at least two analog to digital inputs each one connected to the respective photo detectors 40 and 42 respectively. The controller 50 is further provided with a communication interface (not shown) for interacting with a main controller of a fluidic system wherein the monitor system 10 is incorporated or directly with a user interface in case the monitor system 10 is operated as a stand-alone unit.

Figure 2:
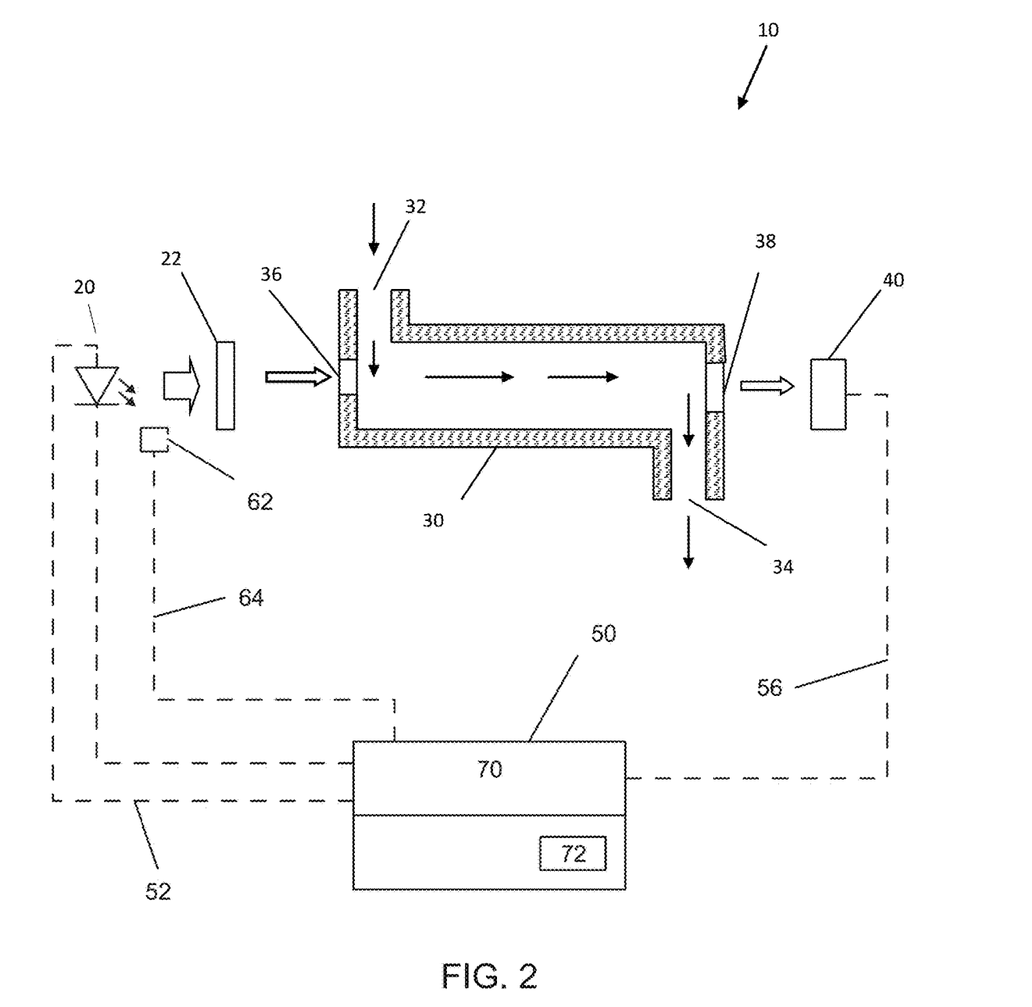
FIG. 2 is a schematic block diagram of an absorption monitor system according to the present invention.

In many applications, it is highly desirable to reduce the overall cost of monitor system 10 of this type, and one way to achieve reduced cost is to remove costly components. FIG. 2 is a schematic representation of a UV-LED based flow cell absorption monitor system 10 according to one embodiment of the present invention. In FIG. 2 the same reference numbers have been used to denote corresponding features as in FIG. 1. In the embodiment of FIG. 2, the reference detector 42 and the associated beam-splitter 24 has been removed in order to reduce cost and complexity of the monitor system 10.

However, by removing the reference detector 42 the output from the monitor system 10 no longer may be actively compensated for fluctuations in light output from the UV-LED 20. In order to make such a reference-less monitor system 10 feasible, the present invention provides means for establishing a stable output from the UV-LED 20.

Figure 3:
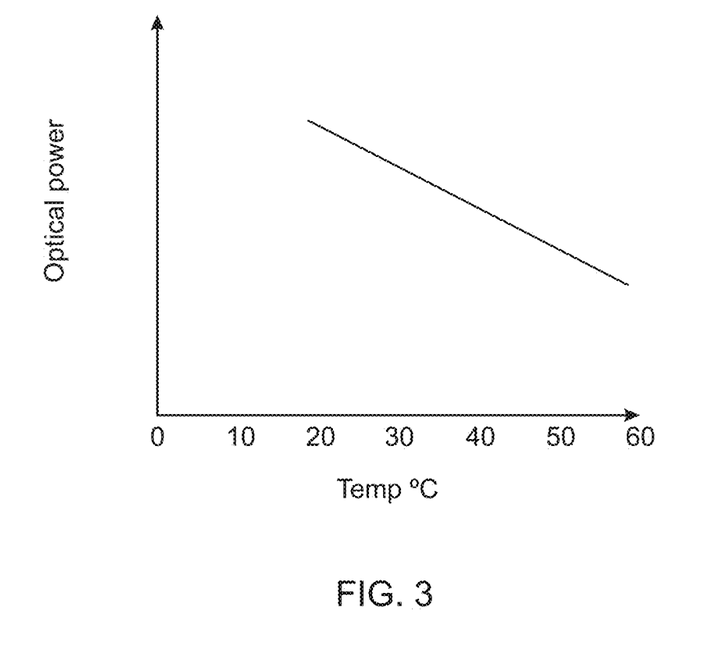
FIG. 3 shows an example of the optical power over a temperature range for a conventional UV-LED.
Figure 4:
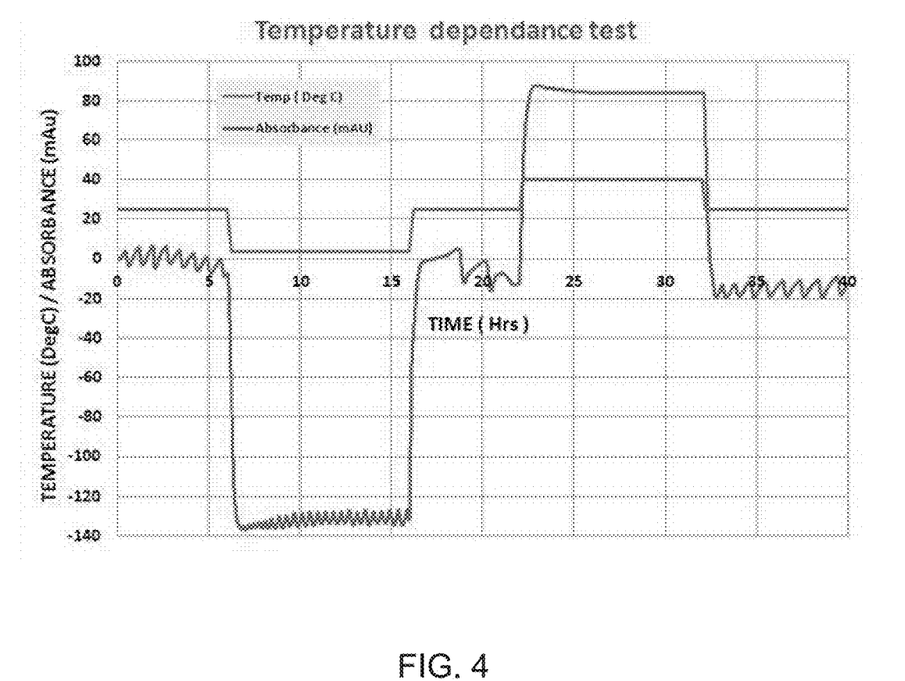
FIG. 4 shows experimental data registered using an uncompensated reference-less monitor system and wherein the temperature of the UV-LED has been changed in steps over time.

One commonly known characteristic of UV-LED's is a significant temperature dependency with respect to the output light intensity. FIG. 3 shows an example of the optical power over a temperature range for a conventional UV-LED. As can be seen in FIG. 3, the output power is essentially inverse linear dependent on the temperature, i.e. the output power decreases linearly as the temperature rises. FIG. 4 shows experimental data registered using an uncompensated reference-less monitor system 10 and wherein the temperature of the UV-LED has been changed in steps over time, and from this figure it is evident that the temperature dependency need to be mitigated in order to achieve a relevant output from the monitor system 10. Therefore in order to compensate for the temperature dependency of the UV-LED 20, the monitor system 10 is provided with a temperature sensor 62 arranged to register the temperature of the UV-LED 20. The temperature sensor 62 may be any suitable sensor, such as a thermo resistor or the like, and it is connected to the controller 50 through a suitable communication line 64. According to one embodiment, the controller 50 is arranged to control the output power of the UV-LED 20 in response to the temperature registered by the temperature sensor 62, e.g. by controlling the bias current fed to the UV-LED 20 in accordance with a predetermined temperature dependency curve, so that a substantially constant output power is achieved from the UV-LED 20. Alternatively, the output power from the UV-LED 20 may be allowed to vary with temperature and the controller 50 is arranged to apply the temperature compensation to the absorption signal registered by the photo-detector 40 based on the predetermined temperature dependency curve. In accordance with one embodiment, the temperature of the UV-LED 20 may be actively controlled at a set temperature. e.g. by a temperature control arrangement (not shown) comprising a heat transfer unit such as a peltier-element or the like for heating and/or cooling the UV-LED 20 in order to preserve the temperature of the UV-LED 20 at a desired setpoint. However, as the monitor system 10 may be used in environments where the surrounding temperature may vary over a relatively broad range, said temperature control arrangement is suitably combined with a temperature compensation using a predetermined temperature dependency curve.

Figure 5:
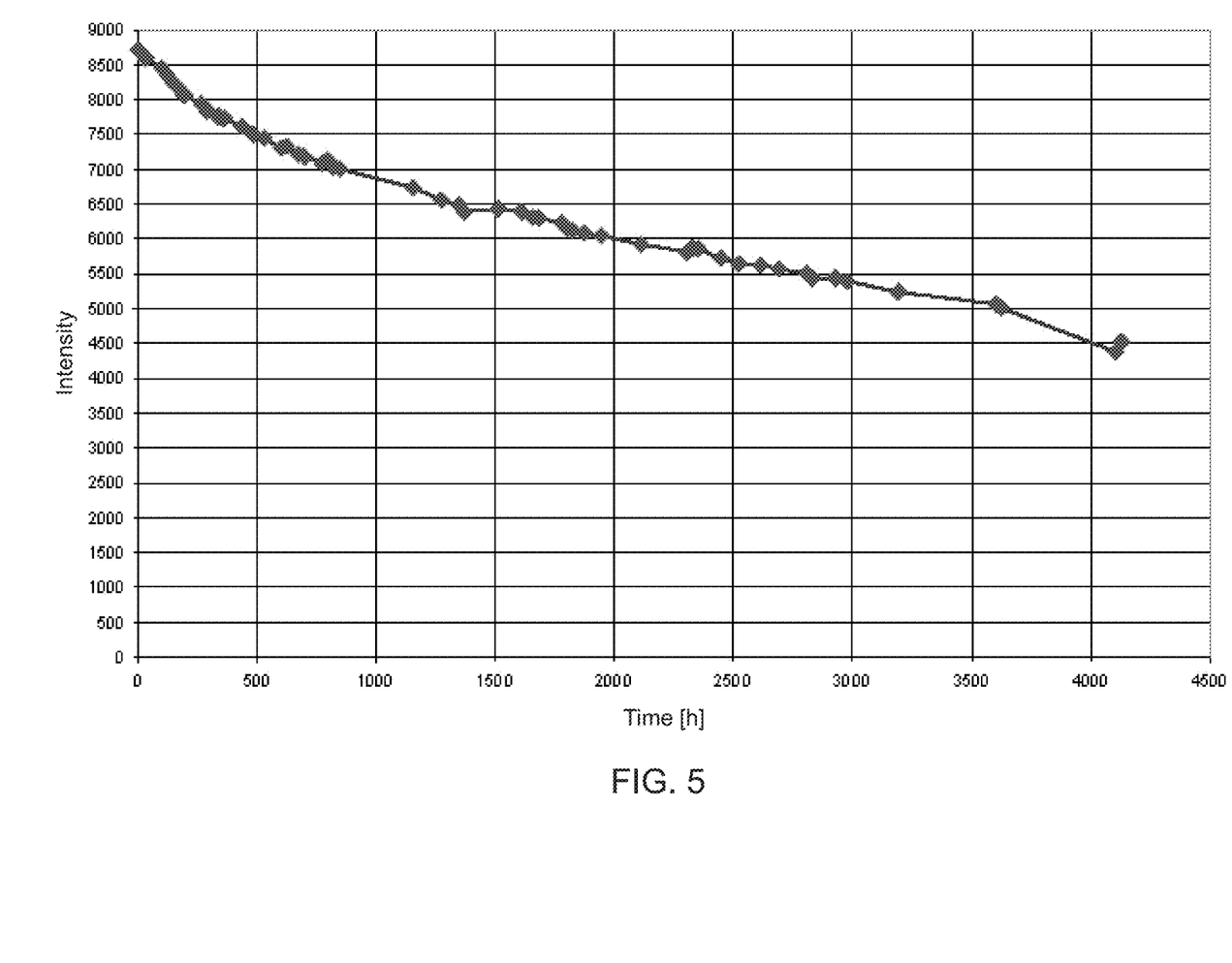
FIG. 5 shows an example of the decreased output-power for a representative UV-LED.

Further, it has been found that the output-power at constant bias-current for commercially available UV-LEDs often decreases over the lifetime of the UV-LED. FIG. 5 shows an example of the decreased output-power for a representative UV-LED. As can be seen in FIG. 5 the output power for this specific UV-LED decreases by approximately 50% over a time span of 4000 hours. It can further be concluded that the rate of decrease is not linear, but variable over time. In the present monitor system 10, the controller 50 is arranged to automatically compensate for the reduction in output power of the UV-LED 20. According to one embodiment, the controller 50 comprises a memory 72 for storing an age correction curve and the controller is further arranged to register and store the total time when the UV-LED 20 is in operation (LED-age) and apply an age correction in accordance with the age correction curve at the registered LED-age. Similar to the temperature correction, the age correction may in one embodiment be implemented by arranging the controller 50 to control the bias current fed to the UV-LED 20 in accordance with the predetermined age correction curve so that a substantially constant output power is achieved from the UV-LED 20 over its lifetime. Alternatively, the output power from the UV-LED 20 may be allowed to vary over the lifetime of the UV LED and the controller 50 is arranged to apply the age correction to the absorption signal registered by the photo-detector 40 based on the predetermined age correction curve. As is indicated by FIG. 5, the age correction curve of the UV-LEDs is suitably determined experimentally, and as different models of UV-LEDs can be expected to show different aging behavior, individual age correction curves may be required for each model that may be used in the monitor system 10. Like in embodiment of FIG. 1, the controller 50 may comprise a digital microcontroller circuit comprising at least one digital to analog output arranged to control the operation of the UV-LED 20 and at least one analog to digital input for the photo detector 40. According to one embodiment, the microcontroller circuit comprises a second analog to digital input arranged to register the bias current driving the UV-LED 20 by registering the voltage drop over a current detection resistor (not shown) connected in series with the UV-LED 20.

In one embodiment, the bias-current of the UV-LED 20 sensed and compared with a predetermined bias-threshold for the current to be consumed after the number of hours of UV LED usage. If the current is not within the predetermined threshold, the current will be varied by the controller 50 to set the registered intensity at the photo-detector side to a predefined level, in one embodiment between 3 V and 4 V. This bias-current adjustment compensates for the drift of UV-LED 20 during previous run. If the registered bias-current indicates that the current is higher than the pre-defined level, the controller 50 may be arranged to issue a warning asking the user to check the flow cell for any unexpected blockage or the like. On detecting successful bias-current level, the bias-current will be stored for this run. Also, the counter to count the number of hours UV LED will be used in this run will be started at this point. This counter is updated throughout the run to log the number of hours UV LED is ON during the run. The voltage at the photo-detector side can be configured for the instrument based on the types of chromatography methods supported by the instrument. The monitor system will also have log of total number of hours the UV LED is used since the installation of new UV-LED. Further, defined cycles of calibration periods can be provided to over-ride the automatic calibration to fine tune the UV readings as per user requirements if required.

The bias-current through the UV-LED 20 is thus a variable component controlled by the controller 50 and the controller 50 is arranged to register current feedback. Also the intensity registered by the photo-detector 40 will be fed to the controller 50. Along with this, the number of hours of UV-LED 20 usage and the registered intensity of the UV-LED 20 during previous run is stored in the memory 72 of the controller to build intelligence to control the UV-LED bias-current at the optimum point during the life cycle of the UV-LED 20. Further, in case the UV-LED is not biased in a predefined range, the lifetime of the UV-LED may be negatively impacted. Thus the above control of the bias level over the lifetime of the UV-LED not only compensates for fluctuations in output power, but also may extend the life of the UV-LED significantly. Also, along with these data, the chromatography method will also be used during the self-calibration to avoid errors in capturing the reference value for the run at this optimum bias point throughout the lifetime of the UV LED 20. The variable bias-current for the UV-LED will allow biasing the UV-LED 20 at optimum point throughout the lifecycle of the UV LED 20 which will increase the life of the UV-LED. Also, the controller 50 will be aware of the bias point and hence will be able to predict the correct voltage range at the detector which will help in eliminating errors in reference due to absorbance by the presence of materials in the flow cell. The intelligence in capturing and verifying the reference signal will reduce the error in UV readings.

According to one embodiment, the controller 50 is arranged to register a reference absorption signal as a part of a detection cycle, and wherein the reference absorption signal is registered for a reference sample with essentially no absorption in the detection band of the monitor system 10. Alternatively, the reference sample may comprise a predetermined concentration of a sample which absorbs light in the detection band. The reference absorption signal may e.g. be registered as an initialization step of a detection cycle wherein a buffer or another reference sample is provided in the flow cell, but it may also be registered at other time points during a detection cycle. In case the monitor system 10 is a part of a manual liquid handling system, the user will have to provide the reference sample in the flow cell manually, but in an automated system, the registration of the reference absorption signal may be partly or fully automated. The controller 50 is then arranged to apply a reference correction to the absorption signal registered by the photo detector 40 using the reference absorption signal. In one embodiment, when the reference absorption signal is registered with a reference sample with no absorption, the reference absorption signal may be considered a "background signal" resulting from absorption by other components or e.g. depositions or the like in the flow cell 30, and the reference absorption signal may be subtracted from the registered signal to provide a referenced output signal.

According to one embodiment, the controller 50 may be arranged to use the signal level from the photo-detector 40 for adjusting the bias current of the UV-LED 20 in combination with or instead of the bias-current through the UV-LED 20 to detect and adjust the bias point for the UV LED 20.

Figure 6:
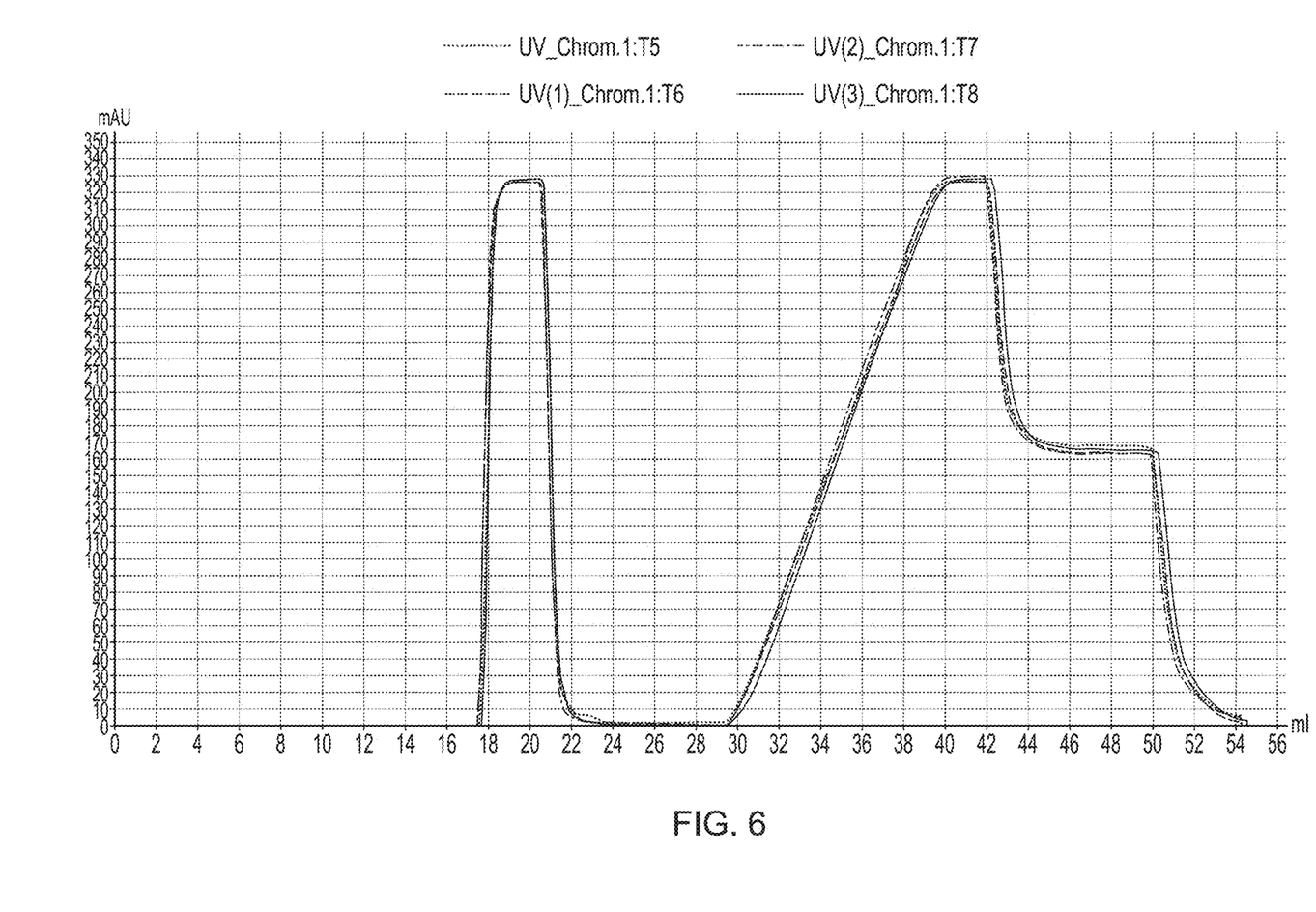
FIG. 6 schematically shows four overlaid UV absorption curves registered using a monitor system of the present invention for the same sample sequence but at different temperatures of the UV-LED.

FIG. 6 schematically shows four overlaid UV absorption curves registered using a monitor system of the present invention for the same sample sequence but at different temperatures of the UV-LED. In the disclosed figure the absorption curves were registered at 3° C., 6° C., 25° C. and 37° C. respectively. Compared with the poor results for a system without temperature compensation of FIG. 4, it is evident that the current solution provides much improved and stable output.

Figure 7:
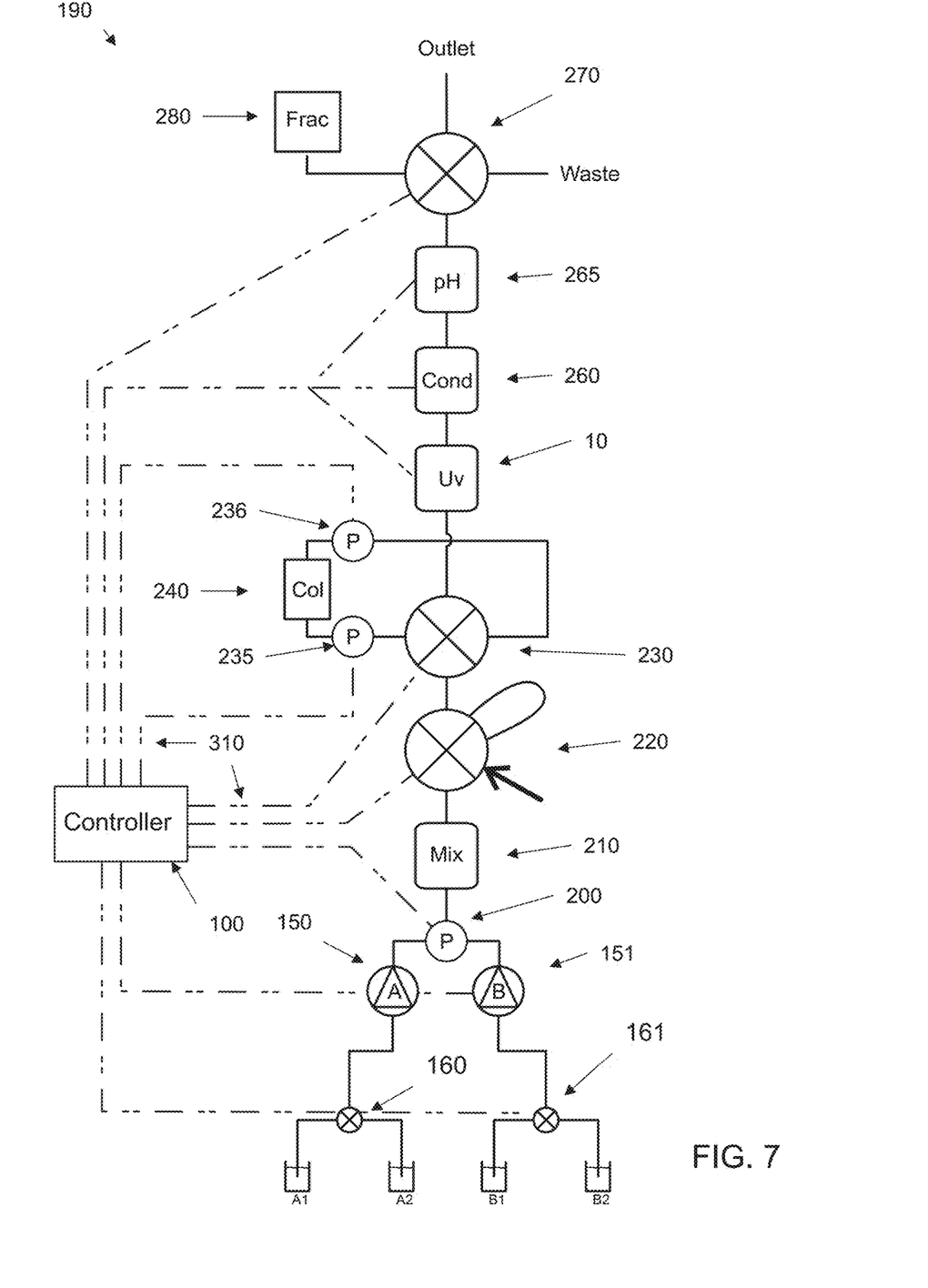
FIG. 7 is a schematic block diagram of a liquid chromatography system comprising an absorption monitor system in accordance with the present invention.

According to one embodiment schematically disclosed in FIG. 7, the monitor system 10 may be comprised as an integral component of a liquid chromatography system 190 e.g. comprising:

two 3-way input-valves 160 and 161, arranged to select the input fluid from fluid sources A1, A2, B1, B2
two system pumps 150 and 151
a pressure sensor 200 for registering the system pressure in the flow path after the system pumps,
a mixer 210 to ensure appropriate mixing of the fluids supplied by the pumps,
an injection valve 220 for injecting a sample into the fluid path,
a column connection valve 230 for selectively connecting/disconnecting a column 240 in the fluid path.
a pre-column pressure sensor 235 and a post-column pressure sensor 236
monitor system 10 in accordance with the present invention for detecting the output from the column
a conductivity monitor 260,
a pH monitor 265,
an output selection valve 270 with two or more output positions, e.g. connected to a fraction collector 280, a waste receptacle or the like and
a system controller 100 connected to pumps and valves for controlling the liquid flow through the system, and to sensors and monitors for monitoring the flow, connections being illustrated by dotted lines 310. In the embodiment of FIG. 7 the controller 50 of the monitor system may either be a dedicated controller in the monitor system, but alternatively its functionality may be integrated in the system controller 100.

The chromatography system of FIG. 7 represents a general example of how a chromatography system may be designed, and other embodiments may be of different design comprising two or more of some components and potentially lack some of said components. According to one embodiment, the chromatography system is a liquid chromatography system.

The invention claimed is:

1. An absorption monitor system comprising
a light source comprising a Light Emitting Diode capable of emitting light in the UV range (UV-LED),
a light detector capable of detecting an absorption signal, wherein the light source and the light detector are arranged so as to define an absorption detection light path there between,
a controller arranged to control the operation of the light source and/or the light detector, and
a temperature sensor for registering the temperature of the UV-LED that is connected to the controller through a communication line,
wherein the absorption monitor system does not comprise a reference light-detector and the fluctuations in light output intensity from the UV-LED is compensated by the controller based on the temperature of the UV-LED, the total time when the UV-LED is in operation (UV-age), and a reference absorption signal stored in the controller.

2. The absorption monitor system of claim 1, wherein the temperature sensor registers the temperature of the UV-LED and the controller is arranged to control the light output intensity from the UV-LED in response to the registered temperature to compensate for fluctuations in light output intensity from the UV-LED due to temperature changes.

3. The absorption monitor system of claim 1, wherein the controller is arranged to register the UV-age of the UV-LED and to control the light output intensity from the UV-LED in response to the registered UV-age to compensate for fluctuations in light output intensity from the UV-LED due to age.

4. The absorption monitor system of claim 1, wherein the controller is arranged to register and store the reference absorption signal for a sample with known absorption and to apply a reference correction to the absorption signal registered by the photo detector using the reference absorption signal.

5. The absorption monitor system of claim 1, wherein the controller is arranged to provide a warning signal when the reference absorption signal exceeds a predefined threshold.

6. The absorption monitor system of claim 1, comprising a flow cell with a fluid flow channel and two opposing windows providing the absorption detection light path there between, one window arranged to receive light from the UV-LED and the other window arranged to output resulting light from the measurement light-path to the light detector.

7. The absorption monitor system of claim 1, wherein the temperature sensor registers the temperature of the UV-LED and the controller is arranged to apply temperature compensation to absorption signal registered by the light detector in response to the registered temperature to compensate for fluctuations in light output intensity from the UV-LED due to temperature changes.

8. The absorption monitor system of claim 1, wherein the controller is arranged to register the UV-age of the UV-LED and to apply age correction to the absorption signal registered by the light detector in response to the registered UV-age to compensate for fluctuations in light output intensity from the UV-LED due to age.

9. The absorption monitor system of claim 1, wherein the UV-LED is biased to increase the life of the LED.

* * * * *